(12) United States Patent
Meyers et al.

(10) Patent No.: US 12,708,767 B2
(45) Date of Patent: Aug. 18, 2026

(54) CONTROL OF FUNCTIONAL ELECTRICAL STIMULATION USING MOTOR UNIT ACTION POTENTIALS

(71) Applicant: Battelle Memorial Institute, Columbus, OH (US)

(72) Inventors: Eric C. Meyers, Columbus, OH (US); Gaurav Sharma, Lewis Center, OH (US); Samuel Colachis, Columbus, OH (US); Nicholas J. Tacca, Columbus, OH (US); Philip T. Putnam, Delaware, OH (US); Michael Darrow, Missouri City, TX (US); Bryan R. Schlink, Westerville, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 808 days.

(21) Appl. No.: 17/984,714

(22) Filed: Nov. 10, 2022

(65) Prior Publication Data

US 2023/0065510 A1 Mar. 2, 2023

Related U.S. Application Data

(63) Continuation-in-part of application No. 16/913,706, filed on Jun. 26, 2020, now Pat. No. 11,524,160.

(Continued)

(51) Int. Cl.
*A61B 5/369* (2021.01)
*A61B 5/00* (2006.01)

(Continued)

(52) U.S. Cl.
CPC ........ *A61N 1/36003* (2013.01); *A61B 5/1104* (2013.01); *A61B 5/1114* (2013.01);

(Continued)

(58) Field of Classification Search
CPC ......... A61B 5/389; A61B 5/256; A61B 5/296; A61N 1/36031; A61N 1/0452
See application file for complete search history.

(56) References Cited

U.S. PATENT DOCUMENTS

2012/0022347 A1 1/2012 Liu
2012/0172682 A1 7/2012 Linderman
2018/0239430 A1 * 8/2018 Tadi ........................ G06F 3/013

FOREIGN PATENT DOCUMENTS

WO WO 2016/196797 A1 12/2016

* cited by examiner

*Primary Examiner* — Michael J D'Abreu
(74) *Attorney, Agent, or Firm* — Lippes Mathias LLP

(57) ABSTRACT

A therapeutic or diagnostic device comprises a wearable electrodes garment including electrodes disposed to contact skin when the wearable electrodes garment is worn, and an electronic controller operatively connected with the electrodes. The electronic controller is programmed to perform a method including: receiving surface electromyography (EMG) signals via the electrodes and extracting one or more motor unit (MU) action potentials from the surface EMG signals. The method may further include identifying an intended movement based at least on features representing the one or more extracted MU action potentials and delivering functional electrical stimulation (FES) effective to implement the intended movement via the electrodes of the wearable electrodes garment. The method may further include generating a patient performance report based at least on a comparison of features representing the one or more extracted MU action potentials and features representing expected and/or baseline MU action potentials for a known intended movement.

16 Claims, 11 Drawing Sheets

Related U.S. Application Data

(60) Provisional application No. 62/868,317, filed on Jun. 28, 2019.

(51) Int. Cl.
*A61B 5/11* (2006.01)
*A61B 5/395* (2021.01)
*A61B 5/397* (2021.01)
*A61N 1/04* (2006.01)
*A61N 1/36* (2006.01)

(52) U.S. Cl.
CPC ............. *A61B 5/395* (2021.01); *A61B 5/397* (2021.01); *A61B 5/6804* (2013.01); *A61B 5/7267* (2013.01); *A61N 1/0452* (2013.01); *A61N 1/0484* (2013.01); *A61N 1/36031* (2017.08)

| | MUs | PNR (dB) | Mean firing rate (pps) | ISI variability (%) |
|---|---|---|---|---|
| Index | 5 | 34.58±2.57 | 13.50±6.56 | 38.71±18.24 |
| Middle | 3 | 32.86±5.42 | 14.21±3.60 | 35.63±5.56 |
| Ring | 3 | 30.36±3.84 | 14.70±5.97 | 27.63±12.53 |
| Pinky | 3 | 44.23±1.64 | 11.05±8.61 | 31.25±13.08 |
| Thumb | 1 | 45.30 | 11.52 | 32.69 |
| Elbow Flexion | 5 | 34.56±3.62 | 15.56±5.41 | 54.79±20.71 |
| Wrist Flexion | 7 | 31.10±4.32 | 17.42±3.66 | 43.78±6.72 |
| Wrist Pronation | 4 | 33.70±6.55 | 16.08±4.06 | 39.94±5.57 |

Fig. 4

CONTROL OF FUNCTIONAL ELECTRICAL STIMULATION USING MOTOR UNIT ACTION POTENTIALS

CROSS-REFERENCE TO RELATED APPLICATIONS

This application is a continuation-in-part (CIP) of U.S. Ser. No. 16/913,706 filed Jun. 26, 2020 which claims priority to U.S. Provisional Patent Application Ser. No. 62/868,317 filed Jun. 28, 2019, the disclosure of each of which is incorporated herein by reference in its entirety.

BACKGROUND

The following relates to the functional electrical stimulation (FES) arts, electromyography (EMG) arts, EMG controlled FES arts, spinal cord injury (SCI) rehabilitation arts, stroke rehabilitation arts, and related arts.

FES devices apply electrical stimulation via surface or intramuscular electrodes in order to stimulate muscle contraction and consequent motion of an arm, leg, hand, or other body part. Use of surface electrodes, as opposed to intramuscular electrodes, is advantageously painless and non-invasive. In the case of a paralyzed patient, that is, a patient having a paralyzed body part due to spinal cord injury (SCI), stroke debilitation, or some other cause of the paralysis, an FES device operatively connected with the paralyzed body portion has the potential to restore volitional control of the hand, forearm, and wrist.

To do so, however, the patient's volitional intent must be measured and converted into FES control signals. One approach is to employ a brain-computer interface (BCI) which measures electrical activity in the motor cortex of the brain via intracortical electrodes, and decodes volitional intent from measured brain electrical activity. This approach has certain disadvantages, notably the invasive nature of the intracortical electrodes and the complexity of brain electrical activity. Even assuming the electrodes are measuring only motor cortex activity, this activity encompasses volitional intent relating to the entire patient's body. This makes decoding volitional intent as respecting a specific body part (e.g., the wrist, or even more precisely a particular muscle of the wrist) challenging. In the case of a stroke patient, effects of the stroke on brain electrical activity may further complicate the decoding of the brain electrical activity.

Certain improvements are disclosed herein.

BRIEF SUMMARY

In accordance with some illustrative embodiments disclosed herein, a therapeutic or diagnostic device comprises a wearable electrodes garment including electrodes disposed to contact skin when the wearable electrodes garment is worn, and an electronic controller operatively connected with the electrodes. The electronic controller is programmed to perform a method including receiving surface electromyography (EMG) signals via the electrodes and extracting one or more motor unit (MU) action potentials from the surface EMG signals. The method may further include identifying an intended movement based at least on feature representing the one or more extracted MU action potentials and delivering functional electrical stimulation (FES) effective to implement the intended movement via the electrodes of the wearable electrodes garment. The method may further include generating a patient performance report based at least on a comparison of features representing the one or more extracted MU action potentials and features representing expected and/or baseline MU action potentials for a known intended movement.

In accordance with some illustrative embodiments disclosed herein, a therapeutic device comprises a wearable electrodes garment including electrodes disposed to contact skin when the wearable electrodes garment is worn, and electronic controller operatively connected with the electrodes. The electronic processor is programmed to perform a method including: receiving surface EMG signals via the electrodes; extracting one or more MU action potentials from the surface EMG signals; identifying an intended movement based on features including at least features representing the one or more extracted MU action potentials; and delivering FES effective to implement the intended movement via the electrodes of the wearable electrodes garment.

In accordance with some illustrative embodiments disclosed herein, a therapeutic or diagnostic method comprises receiving surface EMG signals via electrodes of a wearable electrodes garment and, using an electronic processor: extracting one or more motor unit (MU) action potentials from the surface EMG signals; and one of (i) identifying an intended movement based at least on the one or more extracted MU action potentials delivering functional electrical stimulation (FES) effective to implement the intended movement via the electrodes of the wearable electrodes garment or (ii) generating a patient performance report based at least on a comparison of the one or more extracted MU action potentials and expected and/or baseline MU action potentials for a known intended movement.

In accordance with some illustrative embodiments disclosed herein, a device comprises a wearable electrodes garment including electrodes disposed to contact skin when the wearable electrodes garment is worn, and an electronic controller operatively connected with the electrodes. The electronic controller is programmed to perform a method including: receiving surface EMG activity via the electrodes; extracting one or more features indicative of MU action potentials from the surface EMG activity; determining start and end times for a cortical motor intended movement based on the one or more features indicative of MU action potentials from the surface EMG activity; and delivering FES effective to implement the cortical motor intended movement via the electrodes of the wearable electrodes garment between the start and end times.

In accordance with some illustrative embodiments disclosed herein, in the device of the immediately preceding paragraph the extracting of one or more features indicative of MU action potentials from the surface EMG activity includes determining desynchronization and resynchronization of cortical motor activity from MU action potential firing compared with a baseline. The start time is determined from the desynchronization, and the end time is determined from the resynchronization.

In accordance with some illustrative embodiments disclosed herein, a method comprises: recording surface EMG activity from a target anatomy of a subject using an electrodes garment worn on the target anatomy and including electrodes disposed to contact skin of the anatomy; recording electroencephalography (EEG) activity of the subject concurrently with the recording of the surface EMG activity; determining cortical motor intended movements of the target anatomy from the recorded EEG activity; and training at least one EMG decoder to decode surface EMG activity to determine at least one cortical motor intended movement of the target anatomy using the recorded surface EMG activity labeled with the cortical motor intended movements of the subject determined from the recorded EEG activity to generate at least one trained EMG decoder.

In accordance with some illustrative embodiments disclosed herein, the method of the immediately preceding paragraph further comprises: recording further surface EMG activity from the target anatomy of the subject using the electrodes garment wherein the further surface EMG activity is recorded without concurrently recording EEG activity; and decoding the further surface EMG activity to determine a further cortical motor intended movement using the at least one trained EMG decoder. In some such embodiments the method further comprises applying FES effective to implement the further motor cortical intended movement to the target anatomy of the target anatomy using the electrodes garment.

In accordance with some illustrative embodiments disclosed herein, a method comprises: recording surface EMG activity from a target anatomy of a subject using an electrodes garment worn on the target anatomy and including electrodes disposed to contact skin of the anatomy; determining information about a cortical motor intended movement of the target anatomy based on the recorded EMG activity; and, based on the determined information, delivering FES effective to implement the cortical motor intended movement via the electrodes of the electrodes garment. The determined information includes at least one of: a start time for the cortical motor intended movement, an end time for the cortical motor intended movement, and/or an FES pulse frequency for the delivered FES. In some embodiments, the determined information includes a start time for the cortical motor intended movement which is determined based on desynchronization of cortical motor activity determined from MU firing extracted from the recorded EMG activity. In some embodiments, the determined information includes an end time for the cortical motor intended movement which is determined based on resynchronization of cortical motor activity determined from MU firing extracted from the recorded EMG activity. In some embodiments, the determined information includes an FES pulse frequency for the delivered FES determined based on a firing frequency of motor unit action potentials extracted from the recorded EMG activity. In some embodiments, the determining of the information about a cortical motor intended movement of the target anatomy based on the recorded EMG activity includes decoding the cortical motor intended movement of the target anatomy by applying an EMG decoder to the EMG activity.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

FIGS. 4-10 present experimental results as described herein.

DETAILED DESCRIPTION

Figure 1:
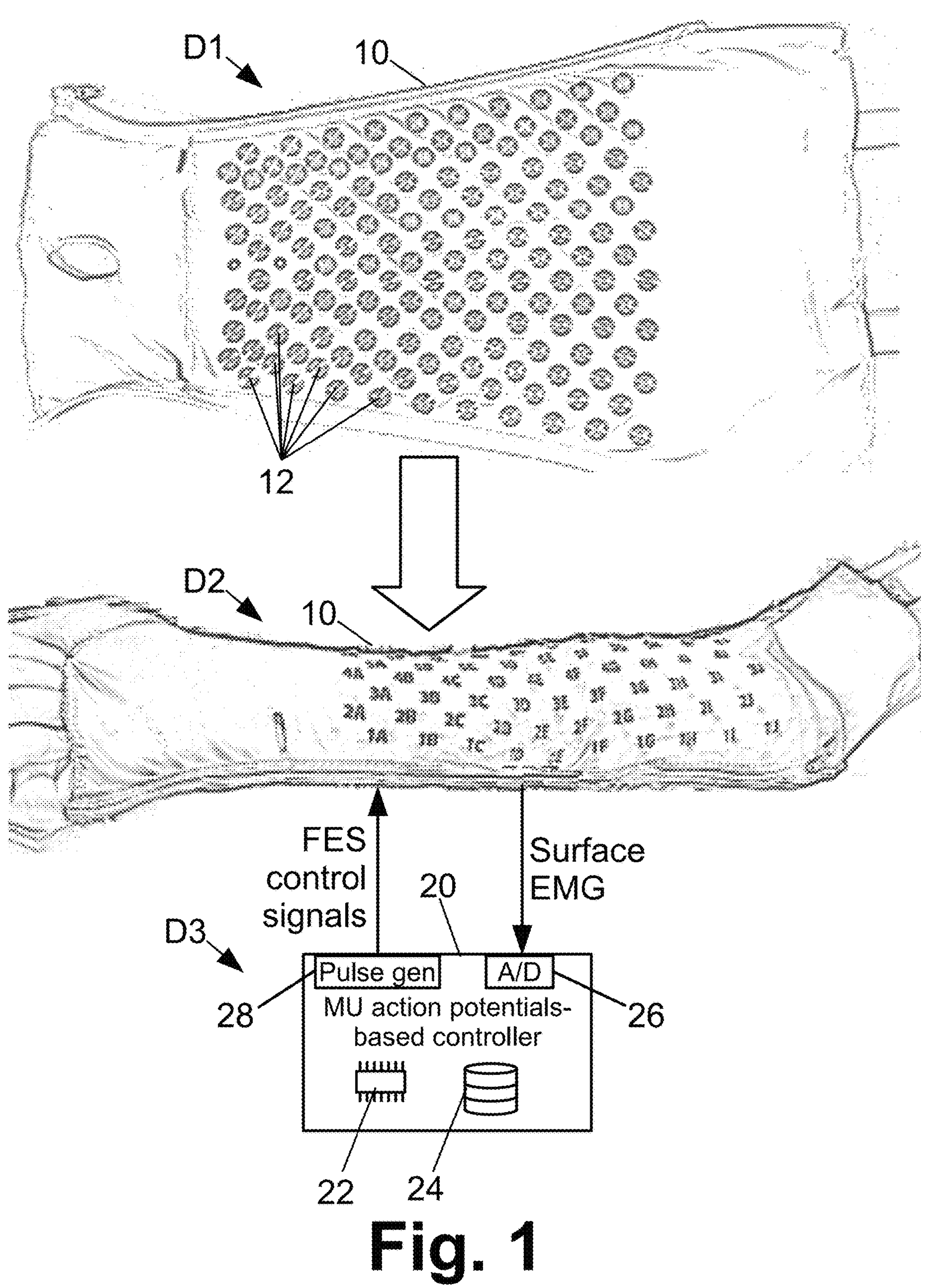
FIG. 1 diagrammatically illustrates a functional electrical stimulation (FES) system.

Another possible approach for measuring volitional intent for driving functional electrical stimulation (FES) is to measure electromyography (EMG) signals at the paralyzed wrist (or other paralyzed body portion). EMG signals are electrical activity produced by skeletal muscles. This approach is premised on the hypothesis that, in spite of the SCI or cause of the paralysis, the patient's volitional intent still generates neural signals to the muscles of the paralyzed body portion, albeit at insufficient strength to stimulate functional muscle contraction. The likelihood of this hypothesis is arguably greater in the case of a stroke patient as compared with an SCI patient; however, experiments have demonstrated that the hypothesis holds for some SCI patients.

However, employing EMG signals for volitional FES control is challenging. If EMG signals are present at all in the paralyzed body part, they are expected to be greatly attenuated compared with EMG signals in a healthy person. This might be countered to some degree by use of intramuscular electrodes (e.g. needle electrodes) to measure the EMG signals, but invasive intramuscular electrodes are often unacceptable to the patient in the case of a wrist, arm, or other flexing body part. Surface EMG signals can be measured using electrodes contacting the skin, which may be more acceptable to the patient. However, the surface EMG signals are weaker than intramuscular EMG signals (and, as noted, the EMG signals are already expected to be greatly attenuated in the paralyzed body part due to the paralysis). A still further difficulty is that the EMG signals can be difficult to decode, as they are not direct metrics of volitional intent but rather are a measure of muscular activity stimulated by the volitional intent. The muscular contractions producing the EMG signals in a paralyzed body part may not simply be attenuated versions of the intended muscular contractions, but instead may include involuntary tremors or other non-volitional muscle activity.

It is recognized herein that measuring motor unit (MU) action potentials provide additional information that can be used in addressing the above-mentioned difficulties. A motor unit is the combination of a motor neuron and the skeletal muscle fibers innervated by that motor neuron. The MU action potential is the electrical signal carried by the motor neuron. Hence, the MU action potential directly captures the volitional intent of the paralyzed patient (albeit likely attenuated due to the paralysis).

The volitional intent to perform a movement of a body part translates, at the MU level, into various parameters such as (in the illustrative examples): (i) the number of MUs recruited to perform the movement; and (ii) the discharge rate (aka firing rate, pulse rate) of the recruited motor units. The number of distinct MU action potentials is extracted by Convolutional Kernel Compensation (CKC) decomposition which has been shown to be effective to extract MU action potentials. See, e.g. Holobar et al., "Accurate identification of motor unit discharge patterns from high-density surface EMG and validation with a novel signal-based performance metric", J. Neural Eng., vol. 11, no. 1, p. 016008, February 2014. The CKC decomposition thus yields the number of MUs recruited as the number of distinct extracted MU action potentials. Other techniques for extracting the MU action potentials are also contemplated, such as wavelet decomposition. Analysis of the discharge pattern of each distinct MU action potential provides information about discharge rate for that MU. More particularly, in the illustrative examples the discharge rate is characterized as a "mean firing rate" or "mean discharge rate" in pulses per second (pps). Additionally, the discharge pattern of each MU action potential is characterized in the illustrative examples by an Interpulse Interval (ISI) variability which is the average ISI of the MU divided by the ISI standard deviation for the MU, in a percentage value. High ISI variability may be an indication of synaptic noise. As a further quality metric, the Pulse-to-Noise Ratio (PNR) in dB is computed for the discharge pattern.

It is recognized herein that effective FES control advantageously relies upon both electromyography (EMG) signals and the MU action potentials extracted as described above. Although EMG signals may not unambiguously correlate with the patient's volitional intent in detail (for example, due to involuntary tremors which also induce EMG signals), it is reasonable to expect that EMG signals will predominantly arise from the muscles that the patient intends to contract. For example, if the patient's volitional intent is to move the index finger, then the EMG signals should predominantly arise from the index finger, and not (for example) from the thumb.

On the other hand, once regions of high neural activity have been identified, this serves as prior knowledge for analyzing the MU action potentials to more precisely decode the particular type of movement that is intended by the patient. For example, a small number of MU action potentials (corresponding to a small number of recruited MUs) and a low discharge rate for those MU action potentials suggests the patient intends to perform a precisely controlled but low force action. Conversely, a high number of MU action potentials with high discharge rates suggests the patient intends to perform a coarse movement with a larger force. Hence, for example, if the EMG decoding indicates the patient intends to move the index finger and the number of MU action potentials is low and have low discharge frequencies, it may be determined that the patient intends to lightly tap something with the index finger; whereas, if the EMG decoding indicates the patient intends to move the index finger and the number of MU action potentials is high and have high discharge frequencies, it may be determined that the patient intends to strongly grasp something using the index finger. The MU actions potential features can be used instead of, or together with, decoded EMG signals for identifying the type and force of movement intended by the patient.

With reference to FIG. 1, an illustrative wearable electrodes garment 10 comprises a sleeve designed to be worn around the forearm of a patient. The electrodes sleeve 10 is shown unwrapped with the side that contacts the forearm in view in the upper drawing D1 of FIG. 1. This view reveals an array of surface electrodes 12 that contact the skin to measure surface potentials on the skin of the forearm. The illustrative embodiment includes 150 electrodes, which are 12 mm diameter stainless steel discs with an interelectrode distance of approximately 15 mm, spanning from the wrist to the elbow joint. This is merely an illustrative layout; in general, the number of electrodes may vary, e.g. 160 electrodes may be used for a larger-size sleeve, or fewer than 150 electrodes may be used for a smaller sized sleeve, or more or fewer electrodes may be used in a sleeve of a given size to provide higher or lower spatial resolution, respectively. Similarly, the mentioned size and specific manufacture of the electrodes is merely a nonlimiting illustrative example. In general, the electrodes should be distributed over the skin contacted by the garment 10 with sufficient number and density to provide high density EMG (HDEMG) measurements at least in regions for which HDEMG measurements are desired. Typically, it is expected that the garment will include at least 50 electrodes to provide HDEMG measurements, although fewer than 50 electrodes is also contemplated. In general, any type of electrode suitable for electrocardiography (ECG), electromyography (EMG), electroencephalography (EEG), or the like can be employed to measure the surface potentials. The middle drawing D2 of FIG. 1 illustrates the electrodes sleeve 10 wrapped onto a forearm of a patient. In this view the electrodes 12 are not visible as they are contacting the skin of the forearm. (However, as seen in the middle drawing D2, the illustrative electrodes sleeve 10 includes two-character digit-letter designators of the underlying electrodes. These designators are optional). It is to be understood that while a forearm sleeve is illustrated, the wearable electrodes garment is suitably configured to be worn on the anatomical body part for which EMG signals are to be detected and/or FES support is to be delivered (e.g. forearm, wrist, hand, leg, ankle, various combinations thereof, and/or so forth). A wrap-around (or otherwise wearable) electrodes garment such as the wrap-around forearm electrodes sleeve 10 of FIG. 1 advantageously can be designed to fit patients of various forearm sizes (and possibly even legs); however, for improved comfort it is contemplated to employ a fitted sleeve, sock, or the like that may not be of a wrap-around design but that is fitted or sized for the particular patient. In the description herein, the term "paralyzed" body part may sometimes be employed as a designation of the body part on which the electrodes garment is worn; however, the term "paralyzed" should be understood to encompass a partially paralyzed body part or a body part that has some motion but not well controlled motion, for example such as may be the case for stroke debilitation.

By way of further non-limiting illustration, some suitable embodiments of the wearable electrodes garment 10 including the electrodes 12 are described in Bouton et al., U.S. Pat. No. 9,884,178 issued Feb. 6, 2018 and Bouton et al., U.S. Pat. No. 9,884,179 issued Feb. 6, 2018, both of which are incorporated herein by reference in their entireties.

With continuing reference to FIG. 1, the lower drawing D3 shows a motor unit (MU) action potentials based electronic controller 20 receives surface EMG signals from the electrodes 12 of the electrodes sleeve 10, and generates FES control signals delivered to the electrodes 12 to perform functional electrical stimulation of the forearm (in the illustrative case) or other body part on which the electrodes garment is worn. The controller 20 also preferably removes any FES evoked artifacts that can corrupt the volitional EMG data. These artifacts can be stimulation induced artifacts, as well as M-wave artifacts due to the movement of the FES-activated muscles. The EMG signals may be received, and the FES signals delivered, via electrical conductors implemented as wires, circuitry of a flexible printed circuit board (PCB) or a rigid PCB or combinations thereof, or the like. For example, the electrodes garment 10 may include a flexible PCB (not shown) via which EMG and FES signals are distributed from/to the electrodes 12. Alternatively, wiring may be woven into fabric of the electrodes garment 10, and/or so forth. The PCB(s), wiring, or other circuitry provides separate channels for each electrode 12, so that the surface EMG signal of each electrode can be individually received and a distinct FES signal sent to each individual electrode. In the illustrative example, there are 150 electrodes and a corresponding 150 channels. It is contemplated to have two or more physical electrodes wired to a single channel, for example if the electrodes are smaller than the spatial resolution desired for a certain region of the anatomy—in such a case the two or more commonly wired electrodes are treated as a single electrode. This kind of differential or bipolar mode can also be advantageous to reduce noise. As a further variant, while in the illustrative example the same set of 150 electrodes are used for both reading surface EMG signals and delivering FES (with suitable time domain multiplexing), in an alternative embodiment it is contemplated to have separate sets of interleaved electrodes for reading the surface EMG signals and delivering the FES. It is additionally/alternatively contemplated to employ wireless connections, for example in one alternative arrangement a wireless connection (such as Bluetooth) may be used to connect the electronic controller 20 with the electrodes garment 10 and a flexible PCB secured with or into the garment may be used to distribute signals to/from the electrodes 12.

In one approach, separate independent sets of EMG and FES electrodes across the interface can be used for sensing and stimulation. The method of choosing these separate sets of EMG and FES electrodes may include a personalized mapping or a consistent standardized set of EMG and FES electrode groups. For example, an injured patient may have sparse EMG signal only in certain parts of the given limb (e.g., due to a stroke or other injury). Therefore, the EMG recording electrode locations may need to be personalized to the specific target muscles that emit a sufficient EMG signal. In this scenarios, other electrodes may not be able to record any EMG signal, and can therefore be excluded or used for separate functions. Furthermore, as an example, standardized independent sets of EMG and FES electrodes can have a fixed location sufficient to record the needed EMG signals and stimulate the needed muscles with FES. This can be achieved by leveraging the known gross anatomy of the target muscle's location or another method.

In another approach, overlapping sets of EMG and FES electrodes can be used for sensing and stimulation. For example, on one electrode EMG can be sensed and used to rapidly produce FES on the same electrode or vice versa. Electronics execute suitably fast switching between sense and stimulation modes and prevents system damage or recording signal artifact (i.e., 'EMG mode' vs. 'FES mode'). The two approaches can be combined or used separately using EMG or FES electrodes on separate electrode array interfaces (e.g., multiple devices distributed over separate body parts). For example, two sleeves can be used on both the right and left arm. EMG can be recorded on a sleeve located on the right arm and used to trigger FES located on the left arm.

The term "surface EMG signals" is used herein to denote the electrical surface potentials received via the electrodes 12. It is recognized herein that these "surface EMG signals" are actually a superposition of EMG signals (that is, electrical activity produced by skeletal muscles) and MU activation potentials (that is, electrical signals delivered by motor neurons to the muscles). However, the electrical activity produced by skeletal muscles is much stronger than the MU activation potentials, and hence the electrical activity produced by skeletal muscles is the dominant signal component of the measured surface potentials. Moreover, the surface potentials measured by surface electrodes disposed over musculature are commonly referred to in the literature as "surface EMG signals". Accordingly, that term is used herein, with the understanding that the surface EMG signals also include a lesser component comprising MU activation potentials.

Figure 2:
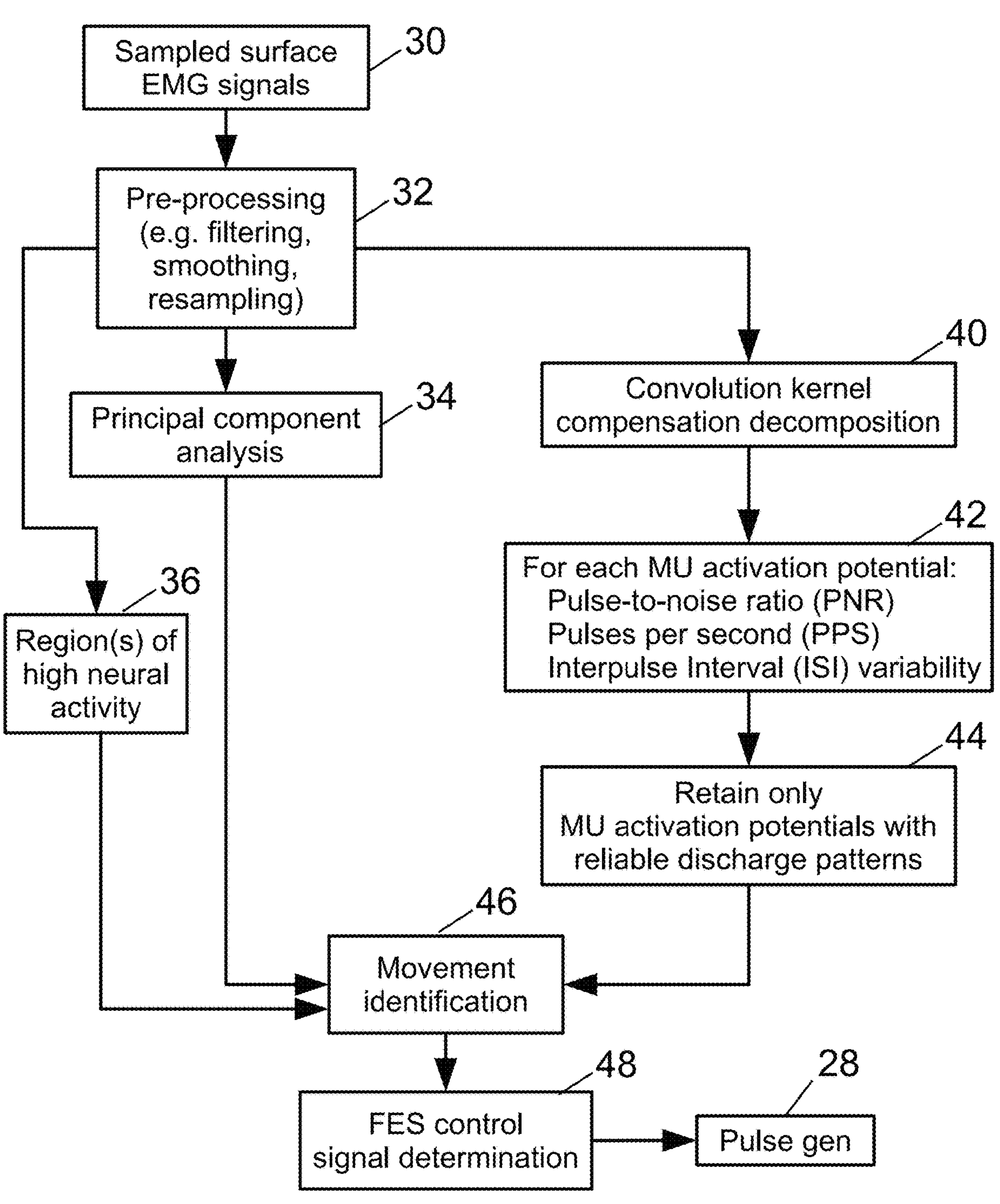
FIG. 2 diagrammatically illustrates a method suitably performed by the controller of the device of FIG. 1 for generating FES signals based on surface potentials measured by the electrodes of the FES from which MU action potentials are extracted.
Figure 3:
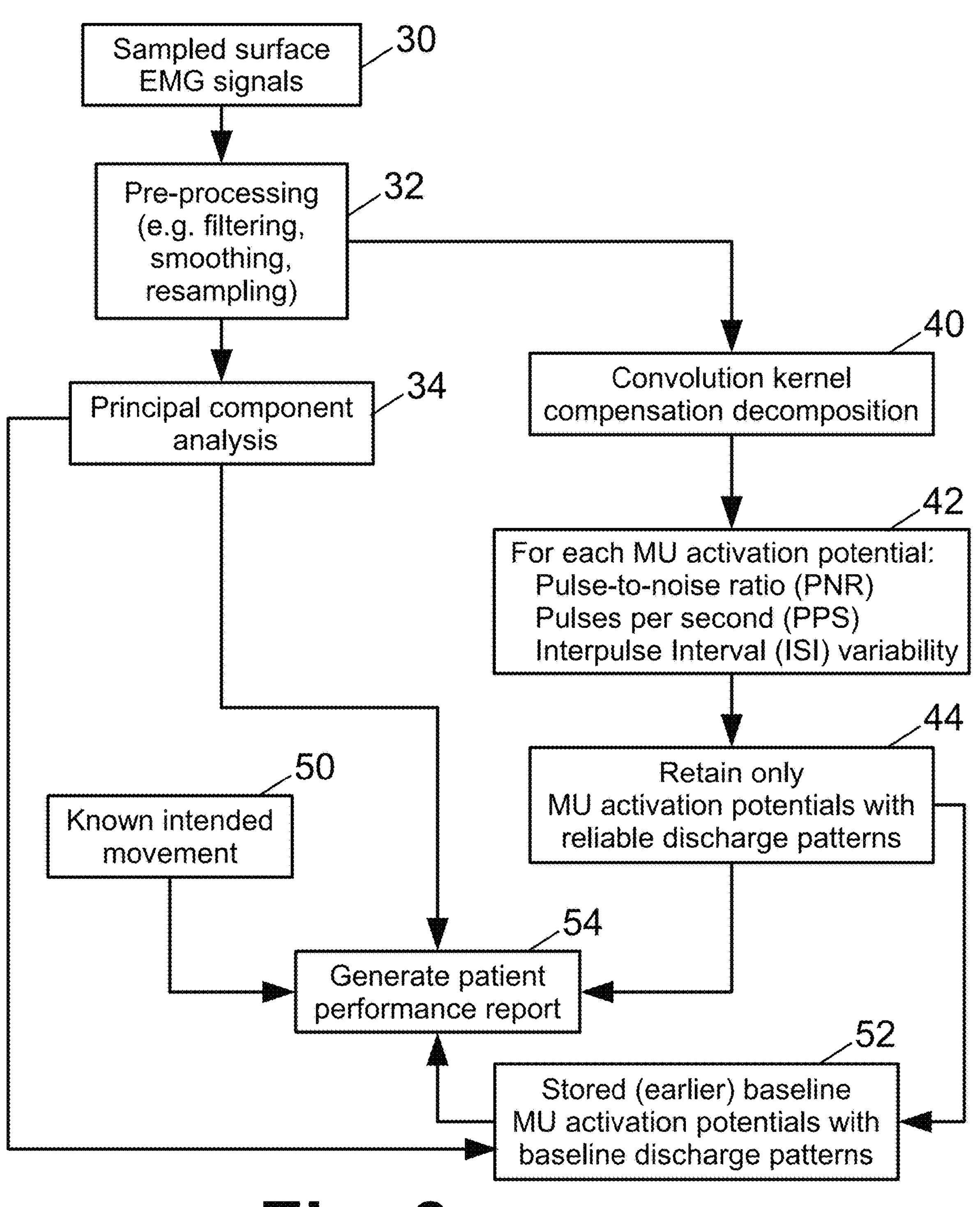
FIG. 3 diagrammatically illustrates a variant method suitably performed by a diagnostic controller and the sleeve of the device of FIG. 1 for assessing performance of an SCI, stroke, or other patient with motor debilitation.

The MU action potentials-based electronic controller 20 is suitably implemented as an electronic device comprising an electronic processor 22 (e.g. a microprocessor or microcontroller or combination of microprocessors and/or microcontrollers) operatively connected with the electrodes 12 and that reads and executes instructions (e.g. software or firmware) stored on a non-transitory storage medium 24 (e.g. a hard disk drive or other magnetic storage medium and/or a flash memory or solid state drive, SSD, or other electronic storage medium and/or an optical disk or other optical storage medium, various combinations thereof, or so forth) to perform the operations as described herein (e.g. with reference to FIG. 2 for FES control embodiments, and/or FIG. 3 for diagnostic embodiments). In other words, the electronic controller 20 is programmed to perform the process of FIG. 2, and/or the process of FIG. 3, and/or variants thereof. The electronic controller 20 further includes analog-to-digital (A/D) circuitry and optionally other electronics (e.g. an amplifier) for receiving and digitizing the surface EMG signals (generically indicated by element 26 in FIG. 1); and a pulse generator 28 for generating FES pulses to be delivered to the electrodes 12. The electronic controller 20 may be integrated into the wearable electrodes garment 10 (e.g. as a small shielded module secured to the exterior of the electrodes garment 10), or may be a belt-worn electronics module connected with the electrodes garment 10 by a wire bundle or cable (optionally connecting via a detachable electrical connector such as a plug, socket, or so forth) or by a Bluetooth or other wireless connection, or may be a desktop computer or the like (in which case patient mobility when wearing the connected electrodes garment is limited).

With reference now to FIG. 2, an illustrative example of a method suitably performed by the electronic controller 20 is described. In the method, the electronic controller 20 receives surface EMG signals 30, which are assumed to be in digital form (e.g. processed by the A/D 26). As previously noted, the surface EMG signals 30 are predominantly electrical activity produced by skeletal muscles, but also include MU activation potentials as a substantially weaker component. In an operation 32, preprocessing such as filtering, smoothing, resampling, or the like is performed to condition the surface EMG signals 30 for further processing. (It is contemplated for some of this preprocessing to be performed in the analog domain prior to the ND 26). In one non-limiting illustrative example, the surface EMG signals are sampled at 30 kHz, bandpass filtered (e.g. with a passband of around a few Hertz to around 7500 Hz or narrower in some embodiments) and resampled at 3 kHz. The preprocessing 32 may also remove FES-induced artifacts. The FES not only causes the muscles to contract, but also creates an artifact that becomes present in the EMG data. This artifact includes a brief period of hardware saturation, followed by an M-wave (response of muscles due to extreme depolarization from FES), followed by an H-wave (response due to the H-reflex). This artifact is suitably removed as part of the preprocessing 32.

The resulting pre-processed surface EMG signals are then processed to generate features drawn from the surface EMG signals (neglecting the impact of the much weaker MU action potentials) and to extract the much weaker MU action potentials which are then also characterized by selected features.

In a non-limiting illustrative example of FIG. 2, the pre-processed surface EMG signals undergo principal component analysis (PCA) 34 and the one, two, three, or possibly more most discriminative (i.e. most principal) components output by the PCA 34 serve as features representing the EMG signals. Additionally, one or more regions of high neural activity 36 may be identified which can provide gross anatomical information useful for identifying the movement.

With continuing reference to FIG. 2, a convolutional kernel compensation (CKC) decomposition 40 is performed on the pre-processed surface EMG signals to generate one or more MU activation potentials. The CKC decomposition is an illustrative example, and more generally other approaches such as Wavelet decomposition can be employed for decomposing EMG and extracting MU activity. See Wang et al., "The Analysis of Surface EMG Signals with the Wavelet-Based Correlation Dimension Method", Computational and Mathematical Methods in Medicine Volume 2014, Article ID 284308 (2014); Li et al., "Wavelet-based detection on MUAPs decomposed from sEMG under different levels of muscle isometric contraction", Proc. of 2017 IEEE International Conference on Robotics and Biomimetics (ROBIO) (2017); Wei et al., "A Wavelet-Based Method to Predict Muscle Forces From Surface Electromyography Signals in Weightlifting", Journal of Bionic Engineering vol. 9 issue 1 pages 48-58 (March 2012). In an operation 42, for each MU activation potential, suitable characteristics (i.e. features) are computed. In the illustrative examples, these include: a discharge rate, specifically in the illustrative examples a mean firing rate (i.e. mean discharge rate) in pulses per second (pps); the Interpulse Interval (ISI) variability in a percentage value; and the Pulse-to-Noise Ratio (PNR) in dB. Optionally, only one or two of these three illustrative characteristics are computed, and/or one or more other characteristics are computed. The choices of units (pps, %, dB) are also illustrative examples and the characteristics may be expressed in other suitable units. In an operation 44, only those MU activation potentials which exhibit a reliable discharge pattern (as indicated by one or more of the characteristics computed in operation 42) are retained. It will be appreciated that the output of the second path via the operation 44 includes (at least) an identification of a set of one or more MUs and the discharge (i.e. firing) rate for each identified MU.

In an operation 46, the features presenting the EMG information (e.g. from the illustrative principal components analysis 34, optionally along with the identified region(s) of high neural activity 36) and the features representing the reliable MU activation potentials (from operations 42, 44) are combined to identify the intended movement. In one approach, the identified region(s) of high neural activity 36 is used to apply a region-specific movement classifier that receives as input the EMG and MU activation potential(s) features (e.g., the principal components from the principal components analysis 34 and the number of MU activation potentials and discharge rates for these as output by the operation 44). More generally, various anatomical regions are associated with movement models parameterized by EMG information and MU activation potential(s) information. The output of the region-specific movement classifier(s) is the identification of the intended movement. By way of some nonlimiting illustrative examples, the region-specific movement classifier(s) may be (optionally multinomial) logistic regression classifiers, SVM classifiers, ANNs, or other ML component(s) that are pre-trained by having the patient (or a cohort of similar patients) perform various volitional movements while measuring surface EMG signals and processing via operations 40, 42, 44 to generate MU activation potential(s) information labeled by the known intended movements that is then used to train the ML component(s) to provide the pre-trained anatomical part-specific movement classifier(s).

In an operation 48, the FES control signals appropriate to implement the intended movement identified in the operation 46 are determined. This can employ the same type of processing employed in brain-computer interface (BCI) driven FES, except that here the input intended movement in provided by the processing/information 32, 34, 36, 40, 42, 44 of FIG. 2 rather than being provided by intracortical data acquired and decoded by a BCI. The output of the operation 46 is used to operate the pulse generator 28 to generate desired FES pulses that are applied by the electrodes 12.

With reference to FIG. 3, in a variant embodiment, the wearable electrodes sleeve or other garment 10 is used as a diagnostic device, rather than for delivery of FES. In other words, in this variant embodiment the electrodes 12 of the electrodes sleeve 10 are used to acquire the surface EMG signals 30, but are not used to deliver FES to the body part. As such, in this variant embodiment the pulse generator 28 of FIG. 1 can be omitted from the electronic controller 20. As shown in FIG. 3, the electronic controller 20 of this variant embodiment performs the analyses 32, 34, 40, 42, 44 of the sampled surface EMG signals 30 as described with reference to FIG. 2. However, for diagnostic purposes, these analyses are performed on the sampled surface EMG signals 30 acquired while the patient is performing (or attempting/intending to perform) a known intended movement 50. For example, the patient may be asked to touch an object using the index finger, and the surface EMG signals 30 are acquired and analyzed while the patient is performing (or attempting to perform) the action of touching the object using the index finger. Since the intended movement 50 is known, the region identification 36 and the movement identification 46 of the FES delivery embodiment of FIG. 2 are omitted in the diagnostic device of FIG. 3. Instead, the resulting EMG features and the reliable MU activation potentials and corresponding discharge patterns output by the operations 32, 34, 40, 42, 44 are compared with corresponding baseline EMG features and MU activation potentials and baseline discharge patterns 52 for the known intended movement 50. The baseline values 52 are suitably baseline values obtained for the patient in an earlier session. (Accordingly, the presently acquired EMG and MU values are stored on the storage 52 for possible use as a baseline in a subsequent session). Based on the comparison of the current EMG and MU values with the baseline values, a patient performance report 54 is generated for the intended movement 50. In general, the goal of rehabilitation therapy is to observe improvement in the current session compared with the baseline performance 52, and this improvement (or lack of improvement; or degradation in performance compared with the baseline if this is indeed the case) is summarized in the patient performance report 54. The report may also provide trendlines of the performance over a series of sessions so as to graphically represent patient performance over time. In a variant embodiment, the movement identification 46 is omitted, and the generation of the performance report 54 is based only on the comparison of the extracted MU action potentials versus the baseline MU action potentials.

In another diagnostic approach (not shown), expected MU activation potentials with expected discharge patterns are suitably obtained by performing the diagnostic process on healthy patients (e.g., patients who do not have SCI, stroke, or otherwise-produced debilitation of the index finger). The report 54 then provides metrics of how closely the patient's performance, as measured by the EMG information and the reliable MU activation potentials (e.g. the number of recruited MUs) and their characteristics (e.g. PNR, discharge rate, ISI variability of the reliable MU activation signals) matches up with the expected MU activation potentials and expected characteristics. This assessment approach can be used instead of, or in addition to, the illustrated comparison with baseline values 52 from an earlier session.

In some embodiments (including the illustrative embodiments), the therapeutic or diagnostic device does not include a brain-computer interface (BCI), and does not employ intracortical signals in performing the FES therapy or patient performance diagnostics. Alternatively, in other embodiments it is contemplated to augment the MU actions potential and EMG information obtained as disclosed herein with intracortical signals acquired by a suitable intracortical electrode or electrodes array.

In the following, some experimental testing relating to aspects of this disclosure are described.

The study participant was a 32 year old male with a C5 motor and C6 sensory American Spinal Injury Association Impairment Scale B spinal cord injury sustained 14 years prior to the experiment. Data were collected as part of an ongoing intracortical brain-computer interface trial conducted under and FDA Investigational Device Exemption and approved by the University of Pittsburgh Institutional Review Board (NCT01894802). Informed consent was obtained prior to any experimental procedures. Intracortical data were not used in the experiments presented here. The participant had normal strength of the elbow flexors and was able to extend his wrist fully with gravity removed but not against gravity with resistance. He had no volitional movement of the elbow extensors, wrist flexors, finger flexors, or finger abductors.

The participant was seated in front of a monitor and cued to attempt a series of movements involving the digits, hand, wrist, and elbow. Specifically, the subject was instructed to flex/extend each digit, close/open his hand, flex/extend and pronate/supinate his wrist, and flex/extend his elbow.

A sleeve electrode array (Battelle Memorial Institute, Columbus, Ohio) containing 150 electrodes was used to measure EMG activity in the extensor and flexor muscles of the forearm during each of the movement trials (FIG. 1, upper and middle drawings D1 and D2). The electrodes were 12 mm diameter stainless steel discs with an interelectrode distance of approximately 15 mm, spanning from the wrist to the elbow joint. Monopolar EMG signals were sampled at 30 kHz. EMG signals were bandpass filtered ($3^{rd}$ order zero-lag Butterworth digital filter, pass-band 10-500 Hz) and resampled at 3000 Hz. Two (open) channels were removed before further processing.

Classification of five digit tasks was performed using the filtered and smoothed EMG signals across all 150 channels of the electrode array. For this analysis, the raw EMG signals were band-pass filtered (zero-lag 4th-order Butterworth digital filter, pass-band 75-7500 Hz), smoothed (zero-lag $4^{th}$ order Butterworth digital filter, cutoff frequency 10 Hz), and resampled at 3000 Hz. Principal component analysis (PCA) was performed on the smoothed signal across channels, and two components were found to account for >95% of the variance and used for classification. Multinomial logistic regression was used to classify movements of the five digits over eight movement periods per digit with leave-one-out cross-validation. One set from each fold was used for testing and the remaining seven sets were used for training. This corresponds to a specific embodiment of the operations 32, 34, 36, of FIGS. 2 and 3.

EMG signals were decomposed into the constituent trains of MU action potentials using the convolution kernel compensation algorithm. Only MUs that showed reliable discharge patterns were selected for the analysis. Spike trains were then represented as binary signals. The spike trains extracted from the EMG were used to trigger a bidimensional average of the global surface EMG to extract the MU action potential waveforms for each channel of the grids. After the blind source separation, we further tested the accuracy of the decomposition by checking the individual MU action potential visually. This analysis was performed by an experienced investigator. This corresponds to a specific embodiment of operation 40 of FIGS. 2 and 3, with the selection of only MUs that showed reliable discharge patterns for the analysis corresponding to operation 44 of FIGS. 2 and 3.

Neural connectivity analysis was performed by computing the coherence function between motor neuron discharge timings. From this analysis, common oscillations in the beta band (>20 Hz) are believed to arise from cortical neurons, and the peak at 10 Hz has been related to the tremor frequency, whilst the lower band reflects the effective neural drive to the muscle (<5 Hz). The coherence functions were computed from non-overlapping 1-*s* Hanning windows. The coherence© was averaged across 50 permutations of motor units and transformed to standard z score. For this purpose, we first converted the coherence in Fishers value FZ=a tan h(C). This value was then normalized to the number of segments (L) used to calculate the coherence Z=FZ/(½L) which corresponds to the variance of estimation. The coherence bias was identified as the average coherence value in the frequency range 100-250 Hz.

Estimates of synaptic noise to motor neurons were obtained by computing the variability in the motor unit interpulse intervals (ISIs). ISI variability was the average motor unit ISI divided by the ISI standard deviation for each motor unit. This value was then averaged across all motor units. The results are presented in the "ISI variability (%)" column of the table of FIG. 4.

Figure 5:
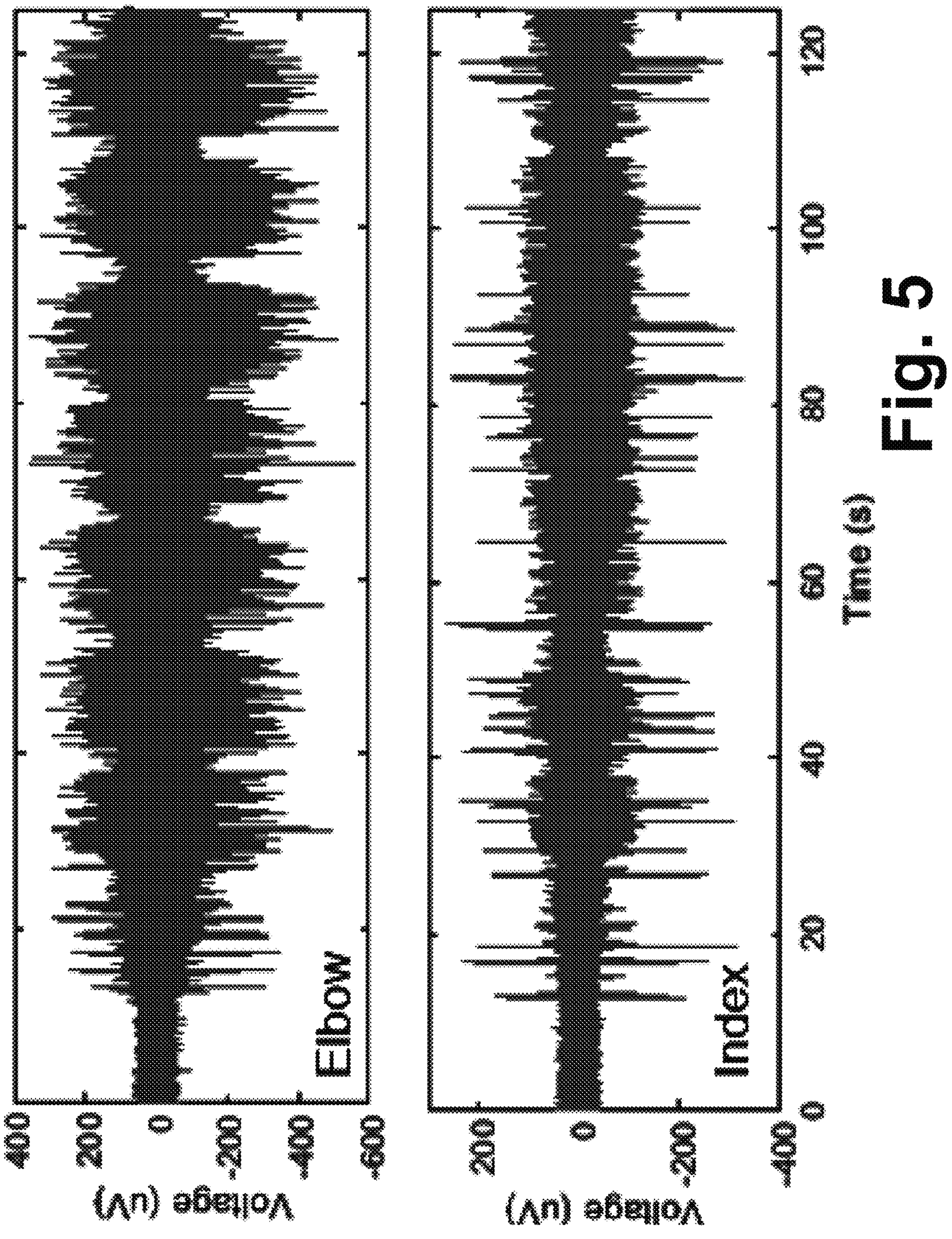

We recorded discernible EMG activity in the paralyzed forearm of an individual with SCI despite a lack of observed movement in the fingers and hand during the tasks. FIG. 5 shows the band-pass filtered EMG signal on a single channels for elbow flexion and extension (top plot of FIG. 5) and index flexion and extension (bottom plot of FIG. 5). The movement periods are easily discriminated from rest during the elbow trial while attempted movements of the index finger are difficult to distinguish visually. However, this myoelectric activity, with minimal post-processing, was robust enough to allow for successful discrimination of all five fingers during attempted flexion and extension movements. It should be noted that the subject attempted the motions for which EMG activity are reported in FIG. 5 without generating detectable motion.

Figure 6:
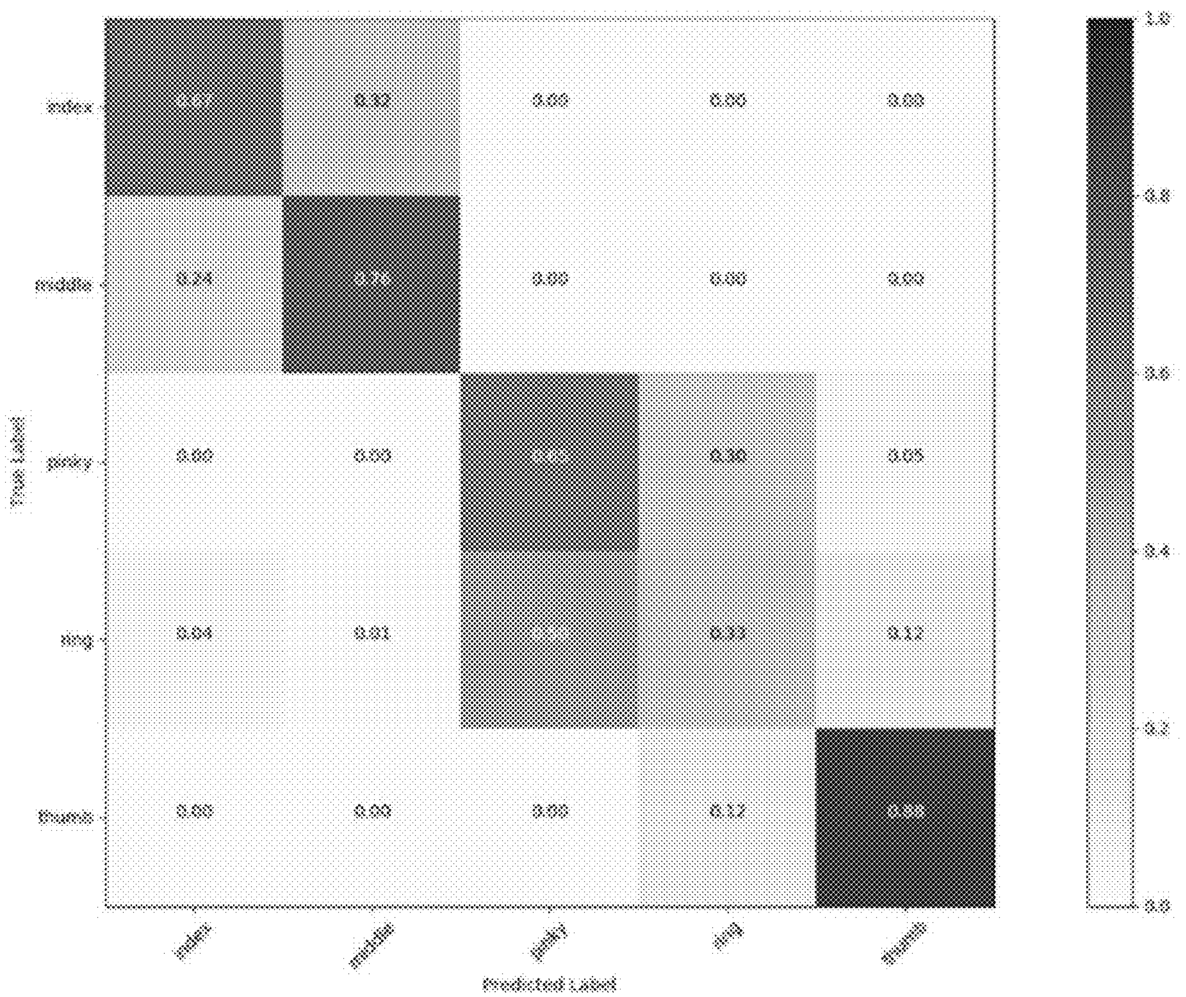

The classification results are shown in FIG. 6, where classification of five digit tasks was performed using multiple linear regression with leave-one-out cross-validation used to classify attempted movements of the five digits during eight movement periods per digit. The accuracy of each decoded movement was calculated as the proportion of samples classified correctly out of all samples of the movement. Thumb finger trials were classified with the highest accuracy (88%), followed by middle (76%), index (67%), pinky (65%), and, lastly, ring (33%). The digits most often confused were ring and pinky and index and middle. A one-sided T-test with alpha 0.05 showed that the classification performs significantly better than chance (p=0.0037). In this step, we have demonstrated that movements can be decoded from residual EMG activity in the absence of visual movement, likely due to the high sensor count across the forearm. It is expected that the electrode sleeve's high channel density and large coverage area will also allow for the classification of more complex hand movements, for example using the MU information gathered in operations 40, 42, 44 of FIGS. 2 and 3. While decoding movements is necessary for the control of neuroprosthetics and assistive devices (e.g., the therapeutic method of FIG. 2), the analysis of extracted MU activity can provide a more thorough description of the physiological changes after neurological damage and throughout the recovery process (e.g., the diagnostic method of FIG. 3).

With returning reference to the table of FIG. 4, the "MUs" column reports the number of identified motor units (MUs) during the individual digit tasks and joint movements. We identified the activity of a relatively large population of motor units. The pulse-to-noise ratio (PNR), average discharge rate, and the interspike interval variability is shown in the "PNR (dB)", "Mean firing rate (pps)", and "ISI variability (%)" columns of the table of FIG. 4, respectively. The computing of these characteristics of the MU action potentials corresponds to a specific embodiment of the operation 42 of FIGS. 2 and 3.

Figure 7:
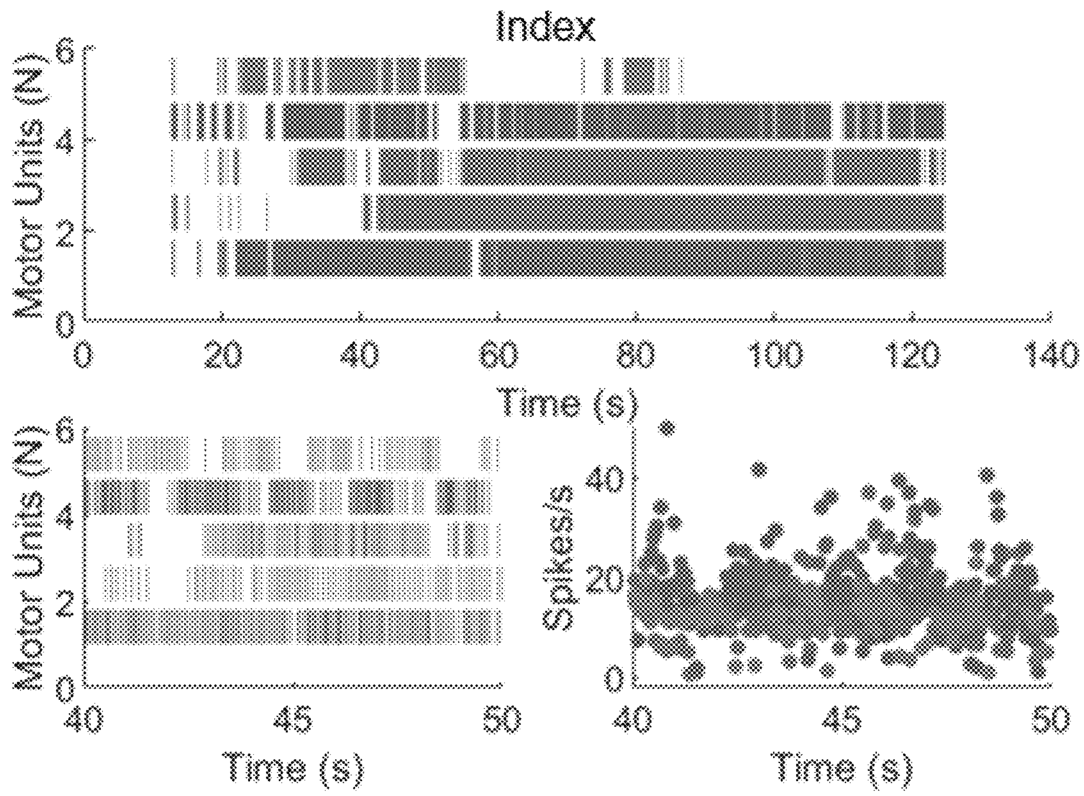
Figure 7:
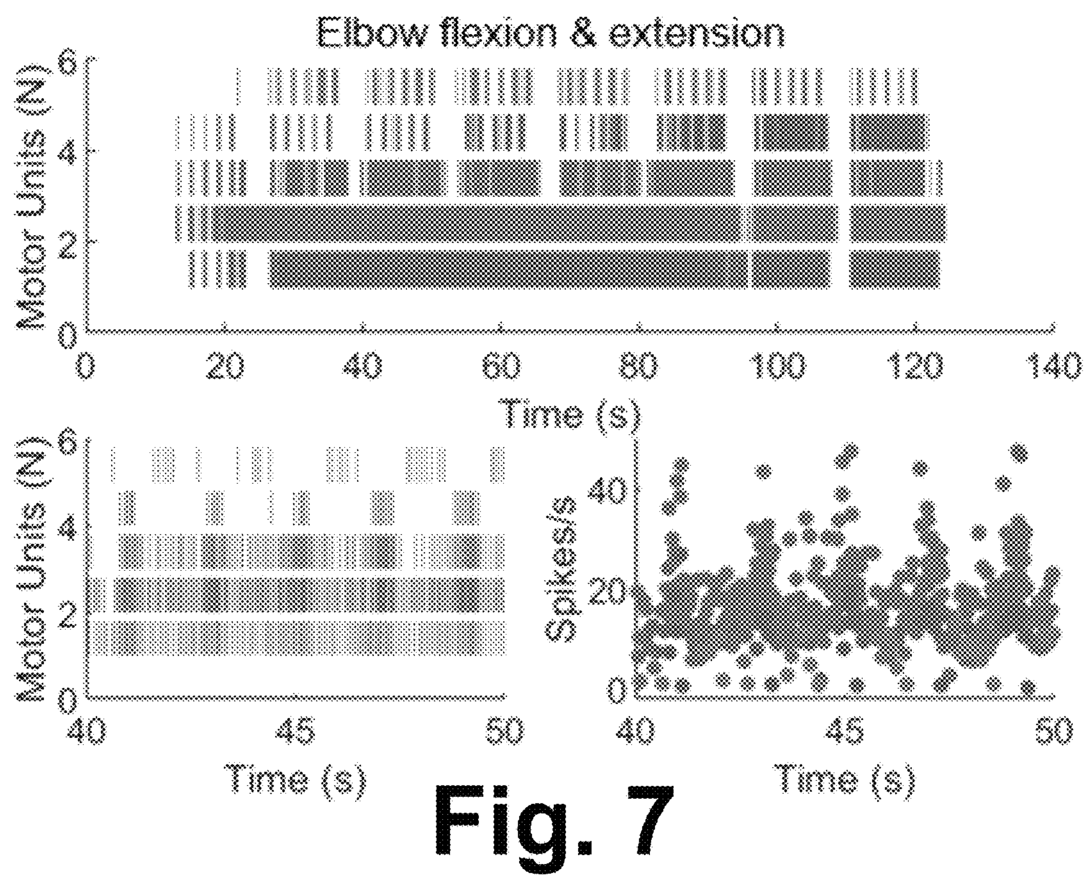
Figure 8:
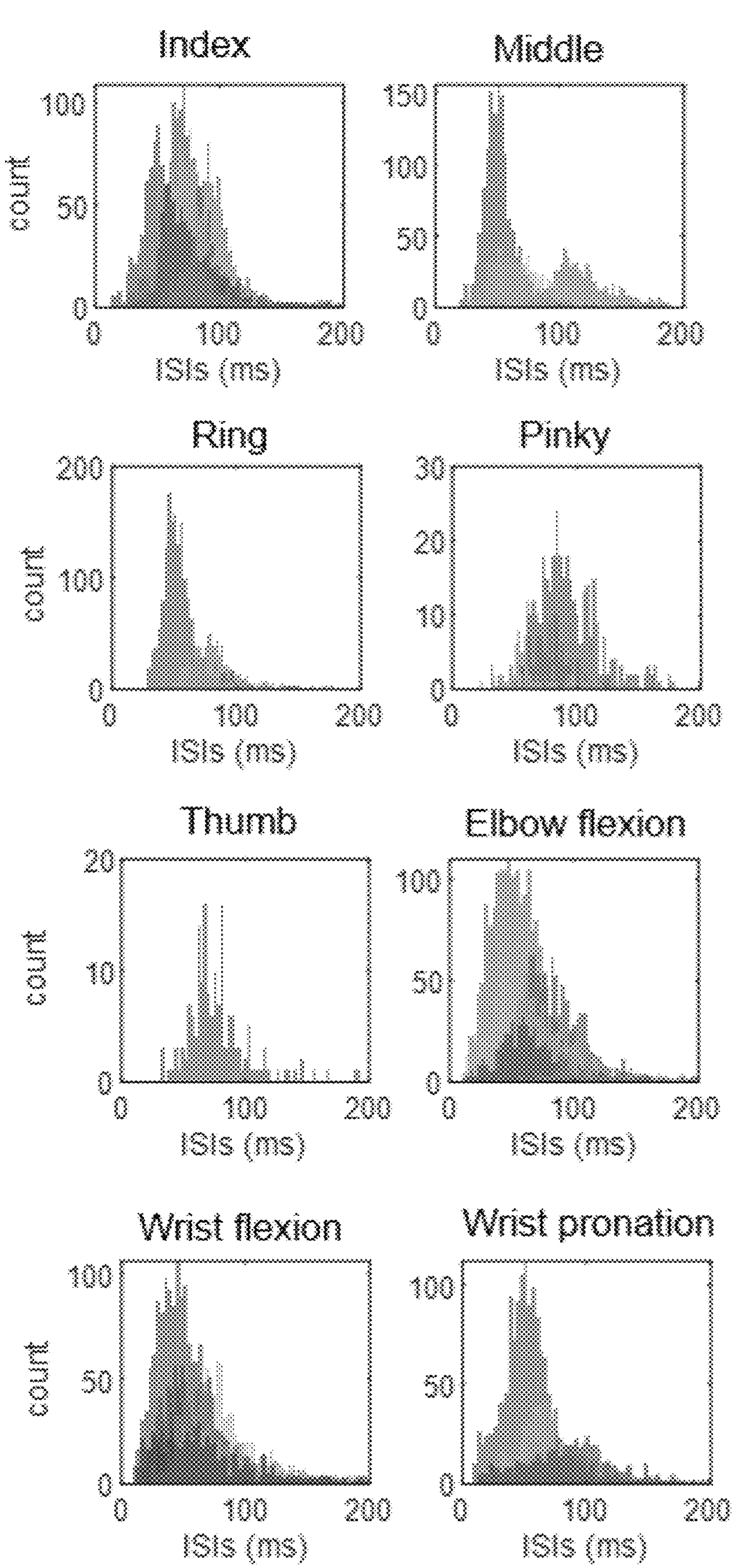
Figure 9:
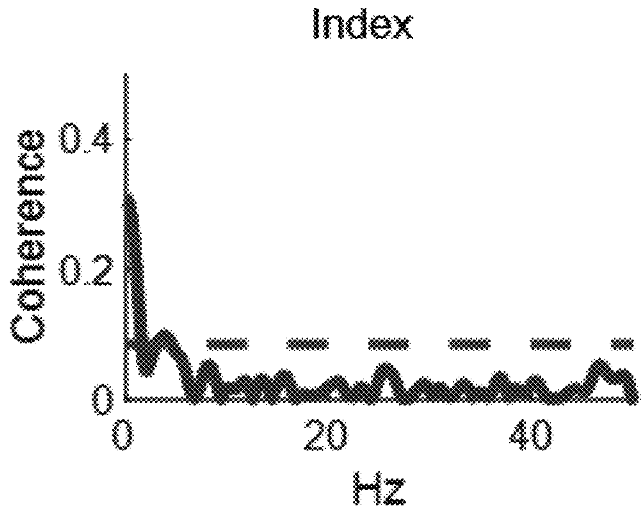
Figure 9:
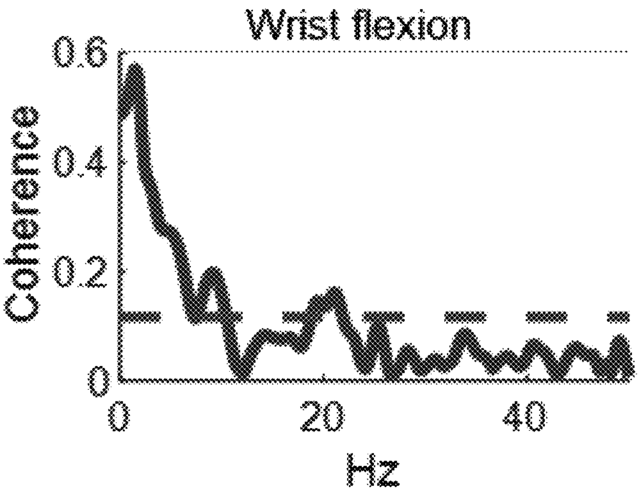
Figure 9:
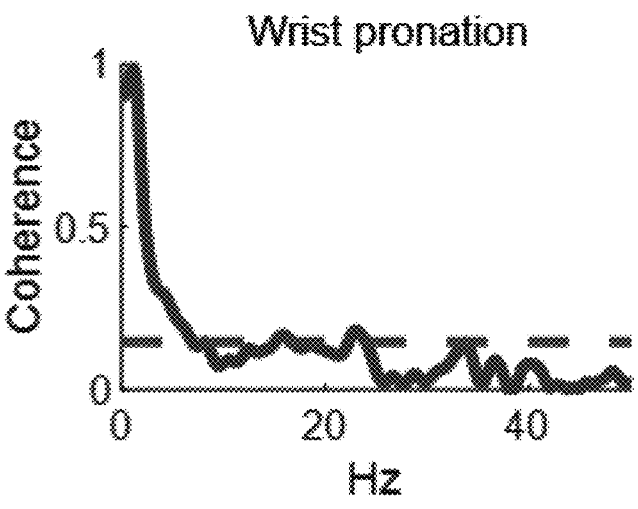

FIGS. 7, 8, and 9 present extracted MU activity in graphical formats, and show the extracted motor unit spike instants for two representative movement trials, index flexion and extension and elbow flexion and extension. Interestingly, some motor units showed a tonic activity whilst other were activated in bursts during the dynamic tasks, reflecting common strategies of joint movements as in intact individuals. Moreover, The average discharge rate and the interspike intervals (see table of FIG. 4) showed similar values as those that have been observed in healthy subjects.

However, the discharge rate variability was significantly higher than what has been observed in healthy individuals (see table of FIG. 4; average across conditions 38.05±8.50%) which may indicate an increase in synaptic noise.

The common input to motor neurons was assessed only for the tasks where we identified greater than three motor units. During wrist flexion and extension, the joint movement with the highest number of identified motor units (number of MUs=7), we observed strong common oscillations in the delta and beta band. These findings indicate that following spinal cord injury (SCI), motor neurons still receive common inputs in the effective bandwidth for force generation (delta band) and receive cortical oscillations common to the pool (beta band).

In some contemplated variants, more complex hand movements may be similarly classified, such as multiple grasp types, and proportional control of those movements with a comparison of input features from both the composite EMG signal and the decomposed MU activity. For example, as noted previously, a higher number of identified MU units with higher discharge rates is expected to correspond to a higher force (albeit possibly with coarser control) intended action; whereas, a smaller number of MU units with lower discharge rates is expected to correspond to a more precisely controlled, lower force intended action. It is further contemplated to leverage analysis of the spiking activity recorded in the motor cortex during the movement tasks (in embodiments in which intracortical activity is recorded, e.g. via an intracortical electrode or electrodes array) for comparison to the decomposed MUs recorded in the musculature.

The described experiments demonstrate that myoelectric activity can be detected and decoded from the forearm of a person with tetraplegia without motion of the hand or fingers, providing a robust control signal for neuroprosthetics and other assistive technologies. This EMG activity can be decomposed into individual MUs, which can provide insight into spinal network reorganization and recovery following neurological injuries, such as SCI and stroke.

In the foregoing, MU features are used to control delivery of FES. In further embodiments disclosed herein, MU frequency modulation is used as an additional control input, which is irrespective of movement. In this way, the control signal reflects the intent of the user formulated in the user's brain. In effect, in these approaches the electrical measurements using the electrodes 12 of the sleeve 10 operate as a peripheral brain computer interface (BCI). This can provide more accurate indication of user intent, especially in applications such as stroke rehabilitation where efferent neural signals from the brain to the muscles may be misdirected due to the effects of the stroke. In some embodiments described herein, the extracted MUs are analyzed to determine motor cortex activity (e.g., efferent neural signals descending from the motor cortex) from the peripheral interface based on modulation of MU firing oscillations. Such coherence (or incoherence) of MU firing enables extraction or decoding of motor cortex commands, so that the sleeve 10 is a peripheral neural interface operating as a BCI, in which modulation of MU firing frequency irrespective of movement outcome leads to additional degree of freedom (DOF) of control.

In some embodiments, MU firing spatial location is used as starting point for FES pattern generation. This facilitates creating personalized and physiologically relevant FES therapy based on MU location/firing intensity. Additionally, this approach can be compared with able-body response or a mirror response of a healthy arm in cases of hemi-paretic stroke to identify differences in MU firing to identify target areas for FES therapy.

These approaches can additionally or alternatively be used to track progress over time, as previously described. Metrics for such tracking may include one or more of: tracking the number of MUs detected for movement generation; weighting of MU activity and firing frequency to a given movement; the relative source activity signal strength; spatial location/shape of motor unit activity; ability for the user to selectively control motor unit firing frequency independent of physical movement; and/or so forth.

In some embodiments, MU spikes are extracted during periods with or without FES. Spikes may for example be identified between FES pulses.

Use of the sleeve 10 as a peripheral BCI is based on the following physiology aspects. Movement is generated via neural drive to the muscle with the signal originating from the motor cortex, which propagates action potentials from motor neurons to a particular motor unit or group of muscle fibers. Motor unit action potentials at the muscle fibers create muscle contraction, thereby producing a desired movement.

In some embodiments disclosed herein, surface EMG recorded with the electrodes 12 of the sleeve 10 placed non-invasively on the skin is made up of a summation of the time course MU action potentials in addition to other confounding signals. It is possible to distinguish between different MUs and MU discharges when using the high-density EMG array 12 using blind source separation techniques. In this way, a spatial and temporal sampling of MU action potentials is determined with non-invasive measures. With a spatial and temporal understanding of motor unit firings, this information is suitably used in assistive technology applications, rehabilitation training and clinical evaluation, as well as neuromuscular electrical stimulation (NMES) pattern generation.

In assistive technology, EMG is decomposed to MU action potentials which can provide spatial and temporal information of motor intent. This is used as a control input for an assistive device such as NMES (e.g., using the electrodes 12 of the sleeve 10), an exoskeleton, or a robotic device. As opposed to using EMG time course and/or spectral features such as the root mean square (RMS) of the signal, MU action potentials provide an additional bandwidth of information to control the sleeve 10 or another assistive device. The frequency of MU firing is modulated independent of physical movement outcome. This volitional control of MU frequency stems from efferent neural signals output by the motor cortex. With spatial and temporal MU firing information, more direct information on cortical motor drive is determined using the sleeve 10 or other peripheral neural interface. This facilitates assisting individuals suffering from motor related disabilities to utilize the electrodes 12 of the sleeve 10 or other peripheral high-density EMG array to control an assistive device with an additional control bandwidth over features extracted from an EMG array. This additional control bandwidth advantageously stems directly from the motor cortex, and thus provides a brain computer interface (BCI) through the non-invasive high-density EMG array 12 placed on an arm, leg, or other peripheral body part.

In clinical applications, muscular activity may be used to trigger functional electrical stimulation (FES) for rehabilitation. Typically, once a certain threshold of RMS activity is reached, FES turns on to evoke a certain movement. However, these approaches can be unsatisfactory in some instances, possibly because the coupling of FES to motor activity does not guarantee that the FES aligns with the participant's true motor intention. Pairing FES with motor intent determined using a BCI can increase neuroplasticity to help improve motor recovery. However, inclusion of a BCI coupled to the patient's brain can be undesirable. In some cases, the electrodes read by the BCI are invasively implanted into (or at least near) the subject's motor cortex, which is undesirable. Use of transcutaneous electrodes avoids use of invasive electrodes, but can degrade the fidelity of the measured brain neural activity, and transcutaneous electrodes attached to the subject's scalp is inconvenient for the subject.

In embodiments disclosed herein, the high-density electrodes array 12 is used to decode the spatial and temporal EMG signal in a way that provides information from the efferent neural signals output by the patient's motor cortex to more accurately decode the subject's motor intention, and stimulates based on that decoded motor intention. In addition to this, decomposing the EMG signal to MU action potentials can provide access to motor cortex activity using the sleeve 10 or other peripheral neural interface. This is expected to assist in ensuring alignment of motor intention decoded from the cortical desynchronization of alpha and/or beta activity (which are biomarkers for movement initiation that can be recorded with EEG from the motor cortex), in addition to a movement determined (e.g. using a classifier) from the RMS signal. This provides an effective (peripheral) BCI-triggered FES through a non-invasive peripheral neural interface that can decode more information than EEG-based BCI systems.

Additionally, the decomposition of the EMG signal into MU action potentials can monitor recovery of a person suffering from movement disabilities over time. By tracking the spatial and temporal firing of MUs, changes over time in the motor activation are evaluated. Some examples include tracking the number of MUs detected for movement generation, weighting of MU activity and firing frequency to a given movement, the relative source activity signal strength, spatial location/shape of MU activity, and ability for the user to selectively control MU firing frequency independent of physical movement. This provides a direct measure of the peripheral motor signal, as well as act as a proxy for the cortical activation for movement generation. Correlating these results from MU activity with functional clinical tests can elucidate neuromechanical biomarkers for tracking rehabilitation progress. This provides a solution to evaluate recovery outside of the clinic via a dual-purpose assistive device (assistance/rehabilitation and rehabilitation monitoring/evaluation).

Using blind source separation to determine spatially where MUs are firing from EMG signal can provide information on where to stimulate muscles to generate movement. By measuring the EMG signal for a desired movement and decomposing that signal to a spatial mapping of different MU action potentials, an initial starting location is determined for FES that corresponds to the physiological activation of the muscles. From there, an automated calibration or manual fine tuning can be used to adjust the FES stimulation pattern to produce the desired movement substantially faster than using a manual process. Additionally, a spatial map for each MU can assist in identifying shifts from session to session, which can then assist in fine-tuning previously calibrated FES patterns based on the motor unit shifts. Still further, the FES provided based on MU action potential location provides a user-specific and physiologically relevant stimulation pattern that is expected to improve rehabilitation efficacy.

Figure 10:
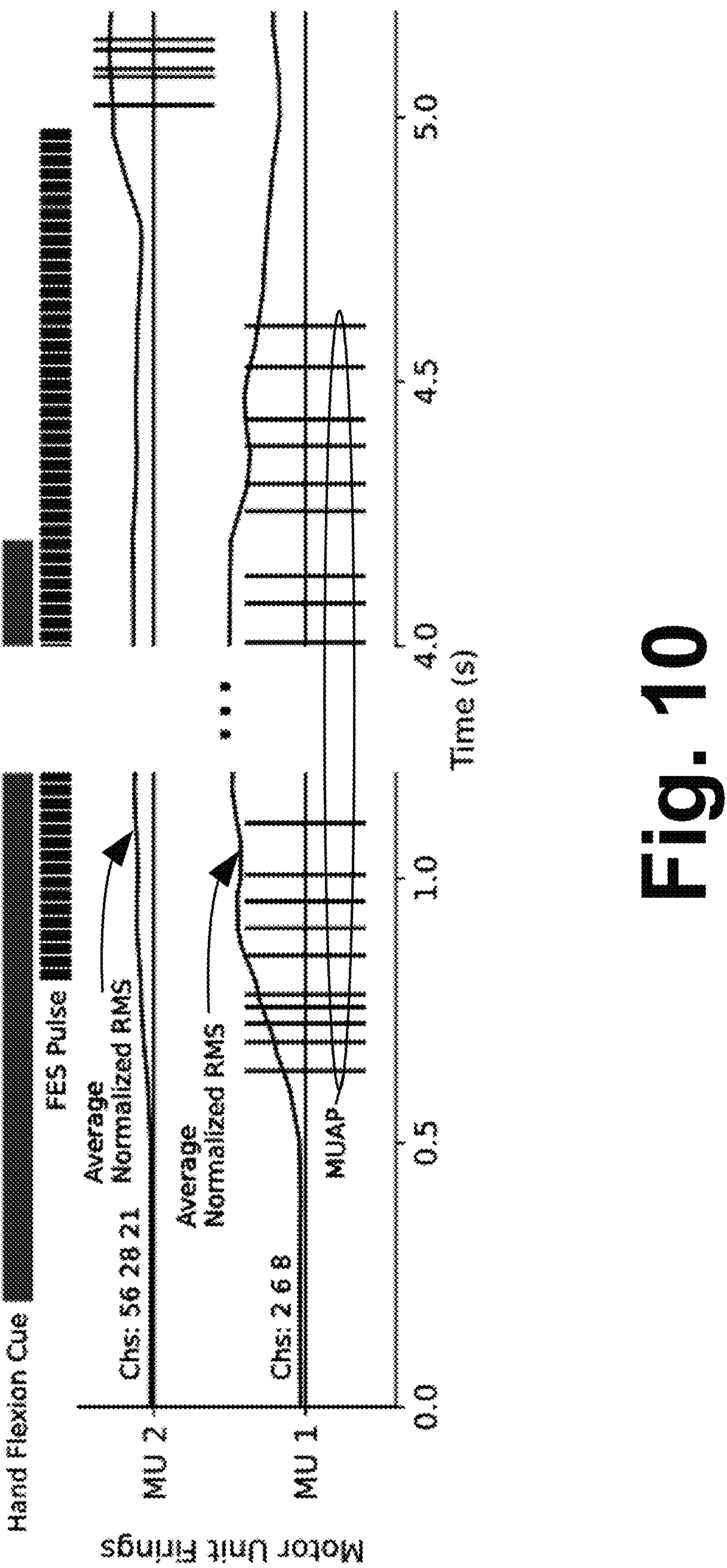

With reference now to FIG. 10, an actually performed example is presented of decomposing an EMG signal recorded from the high-density electrodes array 12 of the sleeve 10 into MU action potential firings. Using the electrode array 12, MU discharges are extracted with and without FES on, thereby providing an on/off signal. Such an on/off signal is not provided by BCI-triggered FES rehabilitation systems. FIG. 10 demonstrates the extraction of MU firings in between FES pulses. FIG. 10 shows a view of select MU firings (labeled as "MUAP", i.e. MU action potentials, in FIG. 10) extracted from a participant suffering from a spinal cord injury using a closed-loop EMG+FES system. A hand flexion cue was given, as diagrammatically indicated in FIG. 10, for the participant to attempt to produce. There was a slight reaction time (less than 0.5 seconds) after the cue onset at which point RMS in flexor channels (labeled as "Average Normalized RMS" in FIG. 10) begins to increase and a flexor MU begins to fire (indicated in FIG. 10 by the "MUAP" events). A decoder picked up the intended movement and initiated stimulation of the participant with FES (indicated by the "FES pulse" bars shown in FIG. 10) to produce a hand flexion movement. MU firings from the flexor MU continued be extracted in between the FES pulses from the EMG signal. Once the hand flexion cue finished, there was a slight reaction time and the RMS (indicated in FIG. 10 as the "Averaged Normalized RMS") began to decrease corresponding to the stopping of the flexor MU discharges, as seen in the right-hand portion of the plot of FIG. 10. After a short delay, the system decoded that the participant was no longer intending to produce the hand flexion and the FES turned off. This then corresponds to a slight increase in extensor RMS and extensor MU firing as the participant opened his hand to return back to the neutral position.

Thus, MU information is used to provide additional control bandwidth based on cortical activity extracted from the electrical activity measured using the electrodes 12 of the sleeve 10 to use with assistive devices. In one contemplated application, by decoding four movement classes from the EMG RMS signal from a person suffering from a spinal cord injury, additional information can be extracted from MU firing frequency that the participant can then learn to control. This provides additional movement classes within the same device that can be decoded so that the user can gain more autonomy. By pairing NMES/FES with motor intention via the neural drive decoded from the feature data of the EMG signal combined with the MU firing frequency that correlates with motor cortical rhythms, the approach acts as a non-invasive peripheral BCI (insofar as brain signals are manifested through MU frequency) with a high-resolution signal.

In some additional actually performed experiments, EMG data from a high-density EMG or EMG+FES electrode array was recorded across various categories of people (able-bodied, stroke patients, SCI patients) across multiple functional movements. Blind source separation was used to spatially locate source activity representing MU discharges. Once a certain threshold of source activity was reached, a spike occurred corresponding to a MU action potential. Different MUs activate different muscle fibers that correspond to muscle activation for a particular movement. The frequency of firing corresponds to the relative activation of the muscle fibers.

Electrical stimulation to generate FES not only assists in the production of movements but also drives lasting cortical re-organization (neuroplasticity) in individuals with neurological injuries. Pairing FES with voluntary motor commands is beneficial for inducing neuroplasticity and recovery in impaired individuals. One method to do this is to have a therapist ask subject to attempt movements, while manually applying FES. The sleeve 10 is suitably used to decode motor intent and apply FES automatically to create a more synchronous pairing of FES with motor intent. The sleeve 10 records EMG to decode attempted movements, thus avoiding the need for electroencephalogram (EEG) recordings of cortical activity to decode motor intent. It is believed that the direct measurement of cortical motor-intent using EEG provides a tighter synchronization of motor commands with FES-activation of muscles and nerves, facilitating greater corticospinal neuroplasticity. In spite of this possible advantage of EEG compared to EMG, as recognized herein EMG-based devices have practical advantages over EEG including usability, superior decoding of varied movements, and ability to decode relax states. An EMG-based system as disclosed herein infers cortical states to precisely deliver FES so as to simultaneously maximize therapeutic efficacy while avoiding such EEG limitations.

In the following, some further embodiments are disclosed which provide various approaches for using EMG to infer cortical motor-related oscillations.

In one approach, decomposition of MU spiking activity from the surface EMG recording is used to infer cortical motor-related oscillations, and associated event-related decompositions (ERDs) that are indicative of motor intent.

As one illustrative example, the spatial EMG data (e.g. EMG activity strength or power) across the anatomy is used to determine the location or locations of muscles being evoked by the cortical motor intent, as the location or locations of maximum EMG activity are expected to correspond to the anatomical muscles whose activity is the cortical motor intent. Feature(s) indicative of MU action potentials are then derived to determine the start and end of the intent to move. In one approach, desynchronization of cortical motor activity determined from the MU action potentials firing, for example as indicated by a decrease of the alpha band power feature from a baseline value, is detected to determine the start of the intent to move. (In some other embodiments, the beta band power feature is similarly used, or a combination of alpha and beta band power features). Subsequent resynchronization of the MU action potentials firing then indicates the movement is completed. Hence in this example, feature(s) indicative of MU action potentials are used to align the timing (on/off signal), while the spatial EMG strength data across the anatomy is decoded to determine the intended movement itself. This approach beneficially uses the desynchronization and resynchronization of the MU action potentials (or other similar features indicative of MU action potentials) to infer desynchronization and resynchronization of cortical motor activity thereby providing timing information which can be difficult to derive from the EMG data without such MU decomposition due to the EMG data potentially including unrelated content such as involuntary tremors and/or other non-volitional muscle activity. In some embodiments, the FES pulse frequency is determined based on the MU firing frequency. This can be done by training including applying the FES and determining experimentally the optimal FES pulse frequency and comparing with the MU firing frequency feature determined in the EMG decomposition 68. In this way, a relation FES pulse frequency=f (MU firing frequency) can be determined. In this nonlimiting illustrative example, decomposition of MU spiking activity from the surface EMG recording is used to infer cortical motor-related oscillations, and associated event-related decompositions (ERDs) that are indicative of motor intent.

Figure 11:
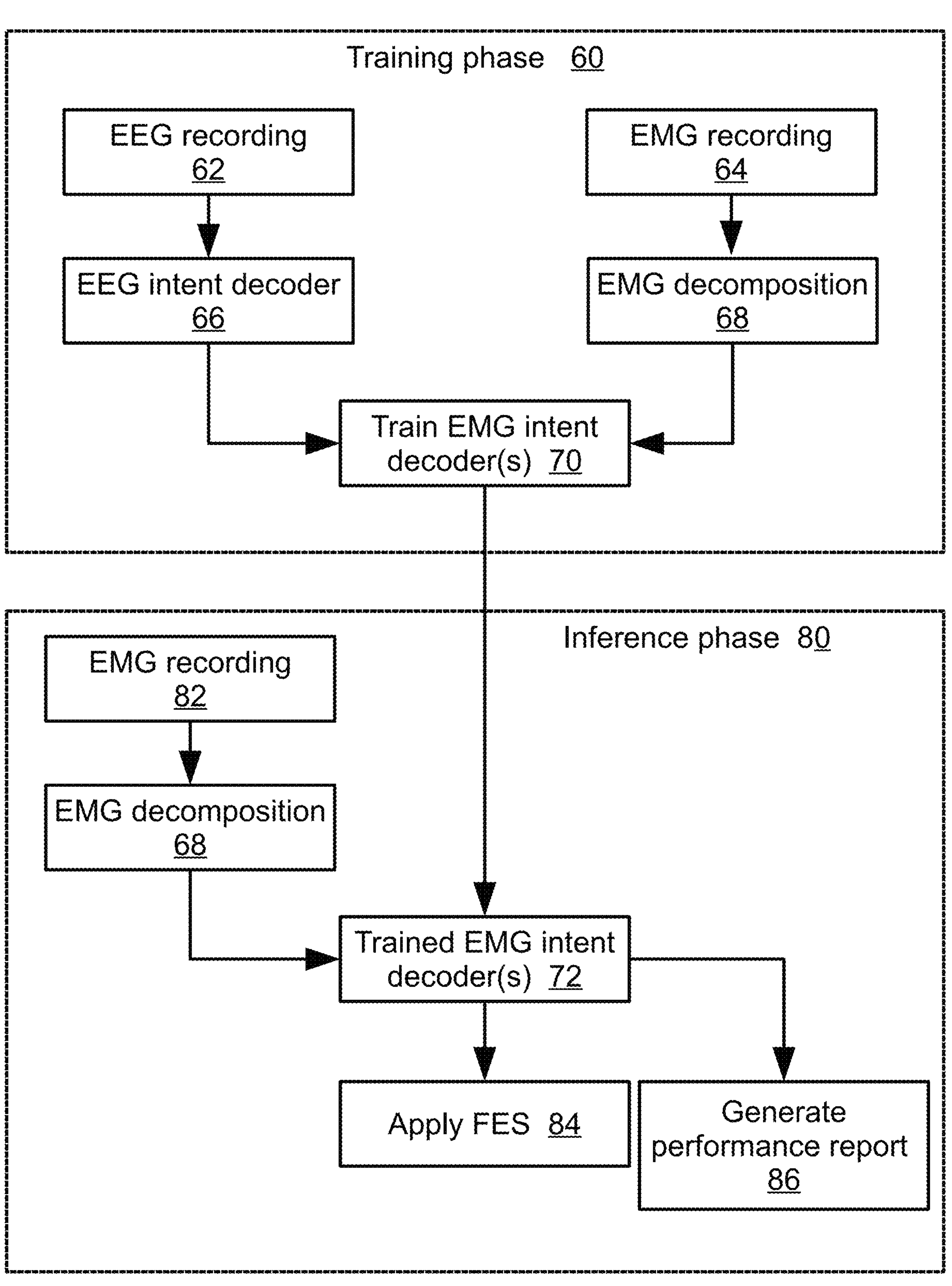
FIG. 11 diagrammatically illustrates a method suitably performed by the controller of the device of FIG. 1 for generating FES signals.

With reference to FIG. 11, in another approach, one or more supervised machine learning (ML) algorithms are trained to predict the cortical motor-related oscillations from the surface EMG activity by using the electroencephalography (EEG) as a "ground truth" during initial calibration sessions where we record simultaneous EEG and EMG. In a training phase 60, EEG recording 62 and concurrent EMG recording 64 are performed while the subject is asked to perform a particular task, such as make a particular hand and/or wrist movement. In an operation 66, the EEG recording is decoded to determine cortical motor intent using a pre-trained EEG decoder, for example such as are commonly used in brain-computer interface (BCI) systems. The output of the operations 62 and 66 constitute measurement of cortical motor-intent using EEG, and this provides a "ground truth" intent for use in the training phase 60. In an operation 68 the EMG is decomposed to generate one or more features indicative of MU action potentials from the surface EMG activity into MU action potentials. For example, the operation 68 may filter one or more frequency bands, such as the alpha band and/or beta band, and compute features as the alpha band power and/or the beta band power. Additionally or alternatively, the features indicative of MU action potentials may include firing frequency or frequencies of one or more MU action potentials. Additional features indicative of MU action potentials from the surface EMG activity may include the pulse-to-noise ratio (PNR), pulses per second (PPS) frequency, interpulse interval (ISI) variability, and so forth. (See FIG. 2, block 42 and related discussion above). The operation 68 may additionally or alternatively decompose features that are not directly associated to specific MU action potentials, such as spatial information about where EMG activity strength is largest. In the operation 68, prior to such feature extraction the raw EMG data may be processed by filtering to remove artifacts such as interference from FES pulses (if applied during the training phase 60), EMG activity at frequencies unlikely to be correlated with cortical motor intent (for example, EMG activity correlative with involuntary tremors), and/or so forth.

The operations 64 and 68 thus provide for recording and decomposition of MU activity potential spiking activity (e.g., power and/or frequency) and/or other features indicative of MU action potentials, optionally along with other EMG-derived information such as spatial locations on the anatomy where the EMG activity is strongest (or, more generally, a spatial distribution of EMG activity strength or power over the area of the arm or other anatomy). In an operation 70, an EMG decoder is trained (or a set of EMG decoders are trained, for example one for each movement whose detection from EMG activity is being trained) using the MU and/or other EMG-based features extracted from the EMG recording in the operation 68, with the EEG-derived intent from the operations 62 and 66 serving as ground truth cortical motor intent for the training. The training may, for example, determine start and end times for the cortical motor intent, and may also optionally determine an optimal FES pulse frequency based on the MU firing frequency as previously discussed. In this embodiment, the ML component is trained to output the optimal FES pulse frequency based on inputs including at least the MU firing frequency feature.

With continuing reference to FIG. 11, the output of the training operation 70 is a trained EMG intent decoder 72 that is used in a subsequent inference phase. Notably, the EEG recording 62 is performed only in the training or calibration phase 60, to provide ground truth cortical motor intent data for the training 70. During the inference phase 80 the subject uses the sleeve 10 to perform activities of daily living (ADL) or so forth. Here, only EMG recording 82 is performed, but not EEG recording. Advantageously this means the subject does not need to have numerous EEG electrodes connected when using the sleeve to assist in ADL. In the inference phase 80, the same EMG decomposition 68 is performed as in the training phase, so as to extract (values for) the same MU and/or other EMG-based features from the EMG recording. These features are input to the trained EMG intent decoder(s) 72 to determine the cortical motor intent, and in an operation 84 the FES to implement that cortical motor intent is applied.

In another application, in an operation 86 the cortical motor intent determined by the EMG intent decoder(s) 72 can be compared with actual performance by the subject (without FES support, or with limited FES support, for example, with the actual performed determined by analysis of video of the subject moving the target anatomy with or without the FES assistance, or using bend sensors attached to the target anatomy to measure such movement), and this information is compiled for various test movements requested of the subject to generate a performance report as per operation 86 of FIG. 11.

By recording simultaneous EEG and EMG in an individual in the operations 62 and 54 during the training phase, the training can directly compare the time at which motor intent can be decoded from each the EEG (e.g., ERDs) and EMG (e.g., root-mean-squared EMG power) relative to the actual movement cue during a calibration process. This comparative analysis is used adjust the timing of FES delivery during EMG decoding of both movement intent and cortical motor-related oscillations to maximize corticospinal plasticity (i.e. triggering the onset of FES stimulation at a time relative to the ERD that is maximally effective for promoting neuroplasticity and recovery).

The disclosed approaches for inferring cortical motor intent from EMG activity can be used in various ways. In assistive technology, multiple MUs are extracted with firings that correspond to different muscle fiber activation. A decoder is trained on the spatial and temporal motor unit firing to control an assistive device. Optionally, the frequency of firings by the user is modulated for an additional control bandwidth independent of the physical movement. Optionally, the FES pulse frequency is determined based on the MU firing frequency.

In clinical rehabilitation and evaluation applications, FES is triggered during rehabilitation exercises that correspond to the neural drive, thus ensuring alignment of FES with motor intention to help promote neuroplasticity for motor recovery. The EMG RMS signal can be used to classify the desired movement, and MU discharge frequency can be used to determine the timing (e.g. start and end of) cortical neural drive (associated with the movement intent formed in the motor cortex). FES for the decoded movement is triggered when there is a desynchronization of alpha and/or beta activity in the motor cortex as determined from the change in MU firing frequency (or, more generally, level of MU firing coherence), and is ended when there is a resynchronization of the alpha and/or beta activity as determined from the change in MU firing coherence.

In another clinical rehabilitation/evaluation application, MU firings are extracted across multiple sessions for individuals to track changes in motor recovery via the activation of MUs. This can include tracking one or more of the following: number of MUs detected for movement generation; weighting of MU activity and firing frequency to a given movement; relative source activity signal strength; spatial location/shape of MU activity; and/or ability for the user to selectively control MU firing frequency independent of physical movement.

In another clinical rehabilitation/evaluation application, these MU activity changes are correlated to functional clinical test results and/or functional magnetic resonance (fMRI) and/or diffusion tensor magnetic resonance imaging (DTI) results to determine neuromechanical biomarkers of recovery. In an example of NMES/FES pattern generation, physiologically relevant NMES/FES stimulation patterns are created based on the spatial location of MUs that activate the relevant muscle fibers. The MU information provides for selection of an initial NMES stimulation pattern as a starting point for an automated calibration method, or as a starting point for manual fine tuning to achieve a desired movement.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method comprising:
recording surface electromyography (EMG) activity from a target anatomy of a subject using an electrodes garment worn on the target anatomy and including electrodes disposed to contact skin of the target anatomy;
recording electroencephalography (EEG) activity of the subject concurrently with the recording of the surface EMG activity;
training at least one EMG decoder to decode surface EMG activity to determine at least one cortical motor intended movement of the target anatomy using the recorded surface EMG activity labeled with the cortical motor intended movements of the subject determined from the recorded EEG activity to generate at least one trained EMG decoder;
recording further surface EMG activity from the target anatomy of the subject using the electrodes garment wherein the further surface EMG activity is recorded without concurrently recording EEG activity;
using the at least one trained EMG decoder, determining information about a cortical motor intended movement of the target anatomy based on the recorded further surface EMG activity; and
based on the determined information, delivering functional electrical stimulation (FES) effective to implement the cortical motor intended movement via the electrodes of the electrodes garment;
wherein the determined information includes at least one of: a start time for the cortical motor intended movement, an end time for the cortical motor intended movement, and/or an FES pulse frequency for the delivered FES.

2. The method of claim 1 wherein:
the determined information includes a start time for the cortical motor intended movement; and
the determining of the information includes determining the start time for the cortical motor intended movement based on desynchronization of cortical motor activity determined from motor unit action potentials firing extracted from the recorded further surface EMG activity.

3. The method of claim 1 wherein:
the determined information includes an end time for the cortical motor intended movement; and
the determining of the information includes determining the end time for the cortical motor intended movement based on resynchronization of cortical motor activity determined from motor unit action potentials firing extracted from the recorded further surface EMG activity.

4. The method of claim 1 wherein:
the determined information includes an FES pulse frequency for the delivered FES; and
the determining of the information includes determining the FES pulse frequency for the delivered FES based on a firing frequency of motor unit action potentials extracted from the recorded further surface EMG activity.

5. The method of claim 1 further comprising:
determining a motor unit (MU) action potentials firing rate from the further surface EMG activity; and
determining an FES pulse frequency based on the MU action potentials firing frequency;
wherein the FES is applied with the determined FES pulse frequency.

6. The method of claim 1 further comprising:
extracting one or more features indicative of MU action potentials from the further surface EMG activity;
determining start and end times for the further cortical motor intended movement based on the one or more features indicative of MU action potentials extracted from the further EMG activity;
wherein the FES is applied between the determined start and end times.

7. The method of claim 1 further comprising:
monitoring movement of the target anatomy to assess an execution of the further cortical motor intended movement; and
generating a performance report for the subject based on the further cortical motor intended movement and the monitoring.

8. The method of claim 1, wherein the EEG signal acts as a ground truth during the training of the at least one EMG decoder.

9. A method comprising:
recording surface electromyography (EMG) activity from a target anatomy of a subject using an electrodes garment worn on the target anatomy and including electrodes disposed to contact skin of the target anatomy;
recording electroencephalography (EEG) activity of the subject concurrently with the recording of the surface EMG activity;
training at least one EMG decoder to decode surface EMG activity to determine at least one cortical motor intended movement of the target anatomy using the recorded surface EMG activity labeled with the cortical motor intended movements of the subject determined from the recorded EEG activity to generate at least one trained EMG decoder;
recording further surface EMG activity from the target anatomy of the subject using the electrodes garment wherein the further surface EMG activity is recorded without concurrently recording EEG activity;
using the at least one trained EMG decoder, determining information about a cortical motor intended movement of the target anatomy based on the further surface EMG activity, the determined information including a start time for the cortical motor intended movement; and
based on the determined information, delivering functional electrical stimulation (FES) effective to implement the cortical motor intended movement via the electrodes of the electrodes garment.

10. The method of claim 9 wherein:
the determining of the information includes determining the start time for the cortical motor intended movement based on desynchronization of cortical motor activity determined from motor unit action potentials firing extracted from the further surface EMG activity.

11. The method of claim 9 wherein:
the determined information further includes an end time for the cortical motor intended movement; and
the determining of the information includes determining the end time for the cortical motor intended movement based on resynchronization of cortical motor activity determined from motor unit action potentials firing extracted from the further surface EMG activity.

12. The method of claim 9 wherein:
the determined information further includes an FES pulse frequency for the delivered FES; and
the determining of the information includes determining the FES pulse frequency for the delivered FES based on a firing frequency of motor unit action potentials extracted from the further surface EMG activity.

13. A method comprising:

recording surface electromyography (EMG) activity from a target anatomy of a subject using an electrodes garment worn on the target anatomy and including electrodes disposed to contact skin of the target anatomy;

recording electroencephalography (EEG) activity of the subject concurrently with the recording of the surface EMG activity;

training at least one EMG decoder to decode surface EMG activity to determine at least one cortical motor intended movement of the target anatomy using the recorded surface EMG activity labeled with the cortical motor intended movements of the subject determined from the recorded EEG activity to generate at least one trained EMG decoder;

recording further surface EMG activity from the target anatomy of the subject using the electrodes garment wherein the further surface EMG activity is recorded without concurrently recording EEG activity;

determining information about a cortical motor intended movement of the target anatomy based on the further surface EMG activity, the determined information including an end time for the cortical motor intended movement; and based on the determined information, delivering functional electrical stimulation (FES) effective to implement the cortical motor intended movement via the electrodes of the electrodes garment.

14. The method of claim 13 wherein:

the determining of the information includes determining the end time for the cortical motor intended movement based on resynchronization of cortical motor activity determined from motor unit action potentials firing extracted from the further surface EMG activity.

15. The method of claim 13 wherein:

the determined information further includes a start time for the cortical motor intended movement; and the determining of the information includes determining the start time for the cortical motor intended movement based on desynchronization of cortical motor activity determined from motor unit action potentials firing extracted from the further surface EMG activity.

16. The method of claim 13 wherein:

the determined information further includes an FES pulse frequency for the delivered FES; and the determining of the information includes determining the FES pulse frequency for the delivered FES based on a firing frequency of motor unit action potentials extracted from the further surface EMG activity.

* * * * *